United States Patent [19]

Puritch et al.

[11] Patent Number: 5,037,654

[45] Date of Patent: Aug. 6, 1991

[54] SUPERSORBENT MATERIAL AS PESTICIDE POTENTIATOR

[75] Inventors: George S. Puritch, Saanichton; Douglas McHarg, Victoria; Roderick Bradbury, Sidney; Wenda Mason, Brentwood Bay, all of Canada

[73] Assignee: Safer, Inc., Newton, Mass.

[21] Appl. No.: 187,589

[22] Filed: Apr. 28, 1988

[51] Int. Cl.$^5$ .............................. A01N 25/08
[52] U.S. Cl. ................................. 424/405; 424/409
[58] Field of Search ........................... 424/405, 409

[56] References Cited

U.S. PATENT DOCUMENTS

| | | | |
|---|---|---|---|
| 2,825,640 | 3/1953 | Northcraft | 71/2.7 |
| 2,988,440 | 7/1961 | Bartlett | 71/2.7 |
| 3,707,807 | 1/1973 | Graves | 47/57.6 |
| 3,885,950 | 7/1975 | Ehrig et al. | 71/85 |
| 3,985,540 | 10/1976 | Fein et al. | 71/67 |
| 4,043,921 | 8/1977 | Hessert et al. | 252/8.5 |
| 4,051,086 | 9/1977 | Reid | 260/17.4 |
| 4,069,161 | 1/1978 | Pogers | 252/8.55 |
| 4,071,508 | 1/1978 | Steckler | 260/79.3 |
| 4,172,066 | 10/1979 | Zweigle et al. | 260/29.6 |
| 4,227,911 | 10/1980 | Leonard et al. | 71/77 |
| 4,617,359 | 10/1986 | Smith | 526/93 |
| 4,622,356 | 11/1986 | Jarovitzky et al. | 524/100 |
| 4,818,534 | 4/1989 | Levy | 424/404 |

FOREIGN PATENT DOCUMENTS 48-10535   4/1973   Japan .

Primary Examiner—Thurman K. Page
Assistant Examiner—Robert H. Harrison
Attorney, Agent, or Firm—Lahive & Cockfield

[57] ABSTRACT

An aqueous pesticidal composition is provided which includes a pesticidally active ingredient in admixture with a polyacrylamide supersorbent material, which may be cross-linked. The pesticidally active ingredient, which may be virtually any commonly used insecticide, herbicide, or fungicide, may be present in the formulation at or below the recommended dosage of the pesticide if used alone. The supersorbent material is present at a concentration in the range of about 0.01 to 0.5 parts by weight per part by weight of formulation. The pesticidal composition of this invention displays synergistic characteristics as the supersorbent, which has no independent pesticidal properties, greatly improves the pesticidal effectiveness of the active pesticidal ingredient with which it is used.

36 Claims, No Drawings

SUPERSORBENT MATERIAL AS PESTICIDE POTENTIATOR

BACKGROUND OF THE INVENTION

This invention relates to pesticide compositions and methods for efficiently and effectively using such compositions. More particularly, the invention relates to an environmentally safe potentiator which improves the activity of such pesticides.

The term "pesticide" is used herein in a generic sense and includes insecticides, fungicides and herbicides. A variety of pesticides are well known and widely used in agricultural, gardening and household applications. Although useful in controlling insect populations as well as the growth of unwanted flora and fungi, many pesticides have been found to be harmful to the environment as well as to humans, other mammals, birds and fish. Indeed, the relatively long term environmental hazards experienced with materials such as DDT and dioxin have increased the awareness of the potentially dangerous environmental impact of widespread use of synthetic pesticides. This has prompted the development of potent, but apparently less dangerous petrochemical-based pesticides. However, these new pesticides are far from ideal as they still pose some threat to environmental safety and may collect in food and fresh water resources.

Efforts have been made to identify naturally occurring materials such as bacterial preparations, naturally occurring fatty acids, and salts of fatty acids which are effective in controlling certain insect, weed and fungi populations. For the most part, however, such pesticidal compounds have been largely ignored, presumably because of their generally lower pesticidal activity.

It would be advantageous to provide an environmentally safe compound which improves pesticidal activity when used in conjunction with a pesticide. Such a compound would be economically and environmentally advantageous in that it would facilitate the use of lesser amounts of a given pesticide, while still achieving effective pesticidal activity.

SUMMARY OF THE INVENTION

It is accordingly an object of the present invention to provide a family of pesticidal compositions which include an environmentally harmless potentiator which serves to improve the activity of the pesticide in the composition. Another object is to provide economical and more environmentally safe pesticidal compositions. A further object of the invention is to provide a method of effectively controlling insect and plant pests while at the same time using smaller amounts of potentially harmful pesticidal compositions. Other objects of the invention will be apparent to those of ordinary skill in the art upon reading the present disclosure.

The present invention comprises a pesticidal composition which includes an environmentally harmless polyacrylamide supersorbent material in admixture with an effective amount of a pesticidal agent or agents. The supersorbent is a typically cross-linked, water dispersable polymer present in the pesticidal formulation in an amount ranging from 0.01 to 0.5 parts by weight. This supersorbent material has a synergistic or potentiating effect on the pesticidal compound as it significantly improves pesticidal potency. In fact, the potency of the pesticidal agent is enhanced to the extent that the pesticide may be used in a concentration below that which is typically recommended for use of the pesticide alone. Despite the use of lesser amounts of the active pesticide ingredient, improved pesticidal potency is observed.

Polyacrylamide supersorbent material may be added to virtually any pesticidal composition to improve its pesticidal effectiveness. It is believed that the supersorbent may act as a humectant, and that its water-retaining property assists in maintaining the pesticidal agent in contact with the surface to which it is applied. Another possible mode of action could be as a binding link (possibly by hydrogen bonding) between pesticides and their target organisms. The polyacrylamide supersorbent material is preferably a high molecular weight, lightly cross-linked polymer (150,000 to 6 million daltons) which is able to absorb and retain from approximately 10 to 600 times its weight in water, preferably at least 40 and more preferably at least 50 times its weight in water.

The pesticidal composition of the present invention typically is used in the form of an aqueous solution. It may be applied to a surface, such as a plant, by spraying techniques well known to those having ordinary skill in the art.

DETAILED DESCRIPTION

The present invention comprises a pesticidal formulation which includes a polyacrylamide supersorbent material, which may be cross-linked, in admixture with a pesticidally effective amount of a pesticide. The supersorbent material enhances the pesticidal potency of the pesticidally active compound or compounds with which it is used, and facilitates the use of lower concentrations of the pesticides.

Virtually any one of the commonly known and used water-borne pesticides may be used to prepare a pesticidal formulation of the present invention. For example, the following insecticides (identified by common name followed by a parenthetical chemical name) may be used in conjunction with polyacrylamide supersorbents to yield effective insecticidal compositions.

Pyrethrin (allethronyl d,l-cis, trans chrysanthemate); Malathion (0,0-dimethyl phosphorodithioate ester of mercapto succinate); Methoprene (isopropyl (2E, 4E)-11-methoxy-3, 7, 11-trimethyl- 2, 4-dodecadienoate); Enstar (2, propynyl (2E, 4E)-3, 7, 11-trimethyl- 2, 4, dodecadienoate); Diflubenzuron (N(((4-chlorophenyl) amino)carbonyl)-2,6-difluorobenzamide); Fluvalinate (N-(2-chloro-4-trifluoromethyl)phenyl)-DL-valine (alpha)-cyano)3-phenoxyphenyl) methyl ester); Cypermethrin ((±)alpha-cyano-3-phenoxybenzyl(±) cis,-trans 3-(2,2-dichlorovinyl)-2,2-dimethyl cyclopropanecarboxylate); *Bacillus thuringiensis kurstaki, Bacillus thuringiensis israelensis; Bacillus thuringiensis tenebrionis*; Vendex (hexakis (beta, beta-dimethylphenethyl)-distannoxane); Carbaryl (1-naphthyl methylcarbamate); Metacil ((4-dimethylaminophenyl-3-methyl-phenyl)-N-methylcarbamate). Other useful insecticides include unsaturated fatty acids and their salts having approximately 18 carbon atoms (such as oleic acid, linoleic acid, linolenic acid and ricinoleic acid) alone, and in admixture with organic esters of phosphoric or thiophosphoric acid and carbamates.

Commonly used herbicides which may be admixed with polyacrylamide supersorbents to formulate an effective pesticidal composition of the present invention include: Glyphosate (N-(phosphonomethyl) glycine);

Alachlor (2,chloro-2,6-diethyl-N-(methoxymethyl)-acetanilide); Ammonium sulfamate; Ammonium nitrate; Ammonium sulfate; Atrazine (2-chloro-4-(ethylamino)-6-(isopropylamino)-s-triazine); Chlorpropham (isopropyl m-chlorocarbanilate); Dicamba (3,6-dichloro-o-anisic acid); Dinoseb (2-sec-butyl-4,6-dinitrophenol); Paraquat (1,1-dimethyl-4-4-bipyridinium); Gramoxone (1,1'-dimethyl-4-4'-bipyridinium dichloride); Picloram (4-amino-3,5,6-trichloropicolinic acid); Simazine (2-chloro-4,6-bis(ethylamino)-s-triazine); Trifluralin [a,a,a-trifluoro-2,6-dinitro-N, N-dipropyl-p-toluidine); 2,4-D ((2, 4-dichlorophenoxy) acetic acid; amine salts of 2, 4-D; mineral salts of 2, 4-D; and esters of 2, 4-D.

Useful herbicide compositions further include straight-chained alpha monocarboxylic acids having from 6 to 18 carbon atoms and their salts alone, e.g., pelargonic acid, a nine carbon straight-chained alpha monocarboxylic acid, or in admixture with ammonium compounds such as ammonium nitrate, ammonium sulfate and ammonium sulfamate.

Commonly used fungicides which may be admixed with polyacrylamide supersorbents to formulate an effective composition of the present invention include: Benomyl (methyl 1-(butylcarbamoyl)-2-benzimidazol carbamate); Captafol (N-(1,1,2,2,-tetrachloroethylthio)-3a,4,7, 7a-tetrahydrophthalimide; Captan (N-(trichloromethylthio)-3a, 4, 7, 7a-tetrahydrophthalimide); Carboxin (2, 3-dihydro-6-methyl-5-phenylcarbamoyl-1,4-oxathiin); Chlorothalonil (tetrachloroisophthalonitrile); Iprodione (3-(3,5-dichlorophenyl)-N-isopropyl-carbomoyl-2, 4-dioxoimidazolidine-1-carboxamide); Maneb (manganese ethylenebisdithiocarbamate); Thiabendazole (2-(4-thiazol-4-yl)benzimidazol); Thiram (tetramethylthiuram disulphide); Zineb (zinc ethylenebisdithiocarbamate).

Other useful fungicides include alpha monocarboxylic acids having from 6 to 12 carbon atoms and their salts, alone or in admixture with other fungicidally active compounds.

The preferred supersorbents for use with the present invention are hydrophilic polyacrylamides. These compounds are polymers of neutralized acrylic acids which may be lightly cross-linked, typically with bisacrylamid. These compounds are able to absorb water to form a relatively stable gel. The cross-linked structure is believed to contribute to the water retention properties of this type of material and to prevent the dissolution of the polymer.

Preferred polyacrylamide supersorbents have a molecular weight ranging from approximately 150,000 daltons up to about 6 million daltons. These hydrophilic polymers may absorb from 10 to about 600 times their weight in water and up to about 30 times their original volume in water. The preferred particle size (dry) of polyacrylamide supersorbent material is less than 60 μm. Larger particles of supersorbent may be used, but generally, the smaller the particle size, the better. Preferred for use in the invention are supersorbents able to absorb and retain at least about 40 times their weight in water.

Examples of preferred polyacrylamide supersorbents which may be used with the present invention include commercially available materials such as those sold under the tradenames Terrasorb AG, Terrasorb GB, and Terrasorb HB, all available from Industrial Services International Inc. of Bradenton, Fla.; Moisture Miser, available from Multiple Concepts Inc. of Chattanooga, Tenn.; Agrosoke, available from Chemical Discoveries of Fort Worth, Tex.; Broadleaf P4, available from Broadleaf Industries of San Diego, Calif.; Cyanamer P-35, Cyanamer A370, Cyanamer P-26 and Cyanamer P-250, all available from Cyanamid Canada Inc. of Niagara Falls, Ontario; Percols 728, Percols 750, Percols 757 and Percol 763, all available from Allied Colloids Canada Inc. of Brampton, Ontario; and Acrylamide, available from Monomer-Polymer and Dajac Laboratories Inc. of Trevose, Pa.

The polyacrylamide supersorbent materials noted above are well known in the art and may be prepared by several different known synthetic techniques. For example, the supersorbents may be prepared as disclosed in U.S. Pat. No. 4,172,066 which is incorporated herein by reference.

The polyacrylamide supersorbent typically is prepared by the polymerization of ethylenically unsaturated amide monomers such as acrylamide, methacrylamide, and/or fumaramide together with about 15 to 30 weight percent ethylenically unsaturated carboxylic acid such as acrylic acid, methacrylic acid, or the like. A relatively small amount (e.g., 10 to 100 parts by weight per million parts by weight of total monomers) of a cross-linking agent is added to the monomer mixture. Exemplary cross-linking agents include N, N'-alkylidene-bis(ethylenically unsaturated amides) such as N, N'-methylene-bis(acrylamide), N, N'-methylene-bis(methacrylamide) and other lower alkylidene-bis(ethylenically unsaturated amides) wherein the alkylide group has from 1 to 4 carbon atoms. Other suitable comonomeric cross-linking agents include divinylarylsulfonates, diethylenically unsaturated diesters, and ethers. Polymerization may be accomplished by a water-in-oil polymerization technique wherein a water-in-oil emulsifying agent is dissolved in an oil phase. A free radical initiator (if used) may be dissolved either in the oil or the monomer. An aqueous solution of monomer or mixed monomers may then be added to the oil phase, with agitation, until emulsified. Where a cross-linking co-monomer is used, it may be added to the oil phase along with the other monomer(s). The reaction may be initiated by purging the reaction medium of oxygen and continuing agitation. The acid component of the lightly cross-linked copolymer is typically neutralized with metal ions, e.g., by adding a base to a solution of the polymer.

The pesticidal formulation of the present invention is generally provided in an aqueous solution which may be sprayed onto a surface, such as a plant, where pesticidal activity is desired. The formulation may be prepared in the form of either an emulsifiable concentrate (e.c.) or a microemulsion (m.e.). While both the emulsifiable concentrate and the microemulsion formulations are effective, the microemulsion is currently preferred.

Emulsifiable concentrate formulations may be prepared by combining the polyacrylamide supersorbent and the desired pesticidal ingredient. Subsequently, this suspension may be combined with pine oil or a vegetable oil, preferably cottonseed oil, to which emulsifiers have been added. This yields a concentrated formulation which may subsequently be diluted to obtain a ready-to-use pesticidal formulation.

A preferred embodiment the emulsifiable concentrate contains approximately 10% polyacrylamide supersorbent, 40% active pesticidal ingredient, 45% pine or cottonseed oil and a total of about 5% emulsifiers. The preferred emulsifiers include blends of anionic and nonionic surfactants, such as those sold under the tradenames Atlox 3404F (2%), Emsorb 6900 (2%) and Atlox 3409F (1%). This concentrated formulation may be diluted with water prior to use to yield a ready-to-use formulation. A typical ready-to-use formulation is one which has been diluted so as to include approximately 0.01 to 0.5 parts polyacrylamide supersorbent per part of active pesticidal ingredient. Preferably, the polyacrylamide is present in the ready-to-use formulation at a concentration of approximately 0.1 part by weight per part of concentrate formulation.

Microemulsion formulations of the present invention may be prepared by suspending the polyacrylamide supersorbent in a suitable amount of an active pesticidal ingredient. Separately, emulsifiers, e.g., Fenopon CO436 and Antarox CO887, are dissolved in a suitable amount of water. The supersorbent/active ingredient suspension and the water/emulsifier solution are then mixed together using a high shear mixing head. This procedure forms a concentrated formulation which may easily be transported and stored. Before use as a pesticide the concentrated microemulsion formulation is diluted with water to such an extent that the supersorbent material is present in the ready-to-use formulation at a concentration of about 0.01 to about 0.5 parts.

The concentration of the active pesticidal ingredient in the diluted composition depends, of course, on the particular pesticide used. One having ordinary skill in the art may easily determine the concentration of a particular pesticide which should be present in a diluted, ready-to-use composition. For example, where pelargonic acid is the active pesticidal ingredient it is preferably present at a concentration of about 0.4 parts per part of the ready-to-use formulation.

Experimentation using various pesticidally active ingredients, with and without polyacrylamide supersorbent, has demonstrated that the formulation of the present invention, which includes polyacrylamide supersorbent in admixture with a pesticide, results in improved pesticidal activity over compositions which use pesticidal active ingredients alone. For example, the herbicide commonly known as paraquat, when used in admixture with 0.1 part polyacrylamide supersorbent per part of formulation, may be used at concentrations which are significantly lower than the lowest recommended dosage of paraquat. In addition, pelargonic acid may be used in lower concentrations in admixture with 0.1 part polyacrylamide supersorbent per part of pelargonic acid formulation (e.g., 0.7% or 0.875%) while still achieving plant damage values which compare favorably to the plant damage values which result when 1.0% solution of pelargonic acid formulation is used alone. Moreover, when the full dosage (1.0%) of pelargonic acid formulation is used with 0.1% polyacrylamide supersorbent, an almost total plant kill is achieved, as compared to approximately 75% plant kill when the same concentration of pelargonic acid formulation is used alone. It is thus expected that the synergistic interaction of the polyacrylamide supersorbent and the pesticide will facilitate the use of concentrations of active pesticidal ingredients lower than those which are typically recommended for virtually all other pesticides.

It is believed that the improved pesticidal potency of the compositions of the present invention results from the ability of the supersorbent to retain water and to maintain the active ingredient in a moist or fluid state and hence in contact with the surface to which it is applied.

The following non-limiting examples demonstrate the unexpected properties of the compositions embodying this invention, and illustrate the generality of those unexpected properties.

In the following examples, unless otherwise noted, an emulsifiable concentrate formulation containing a pesticidally active ingredient and a polyacrylamide supersorbent was prepared and diluted to a ready-to-use formulation. A suspension was prepared which contained 20% polyacrylamide supersorbent (Broadleaf P4) and 80% of a pesticidally active ingredient consisting of pelargonic acid. This suspension was mixed with a solution containing 90% cottonseed oil and 10% emulsifiers. The emulsifier component preferably comprises 4% Atlox 3404F, 4% Emsorb 6900 and 2% Atlox 3409F. After mixing the suspension and the oil solution, an emulsifiable concentrate was prepared. The emulsifiable concentrate was subsequently diluted with water to yield a formulation comprising 0.4% of the pesticidally active ingredient and 0.1% of the Broadleaf P4 polyacrylamide supersorbent.

EXAMPLE 1

Two hundred *Hypochoeris radicata* (false dandelion) plants were treated with the diluted formulation described above (0.7% pesticidal formulation and 0.1% supersorbent), 0.7% pesticidal formulation without supersorbent, or 100% water alone. The plants were placed into temperature and humidity regimes in a randomized complete block design. After about 7 days, the plant damage was assessed and the following results were obtained.

| | % Plant Damage | | | | |
|---|---|---|---|---|---|
| | Warm | | Cold | | Green- |
| Herbicide | Dry | Damp | Dry | Damp | house |
| Pesticidal formulation alone | 9.0% | 13.0% | 16.0% | 8.0% | 23.0% |
| Pesticidal formulation with supersorbent | 64.0% | 56.0% | 21.0% | 15.0% | 54.0% |
| 100% water | 0% | 0% | 0% | 0% | 0% |

EXAMPLE 2

The procedure of Example 1 was followed to prepare an emulsifiable concentrate containing the supersorbent and the pesticidal agent. For the purposes of this example, however, the concentrate was diluted to yield a solution having 0.75% pesticidal formulation and 0.10% supersorbent. Forty *Hypochoeris radicata* (false dandelion) plants were treated with 0.75% pesticidal formulation without supersorbent, a formulation containing 0.75% pesticidal formulation admixed with 0.10% supersorbent, or water. The plants were placed in a greenhouse and after seven days the plant damage was assessed and the following results were obtained.

| Treatment | | % Plant Damage |
|---|---|---|
| pesticidal formulation | (0.75%) | 23.0% |
| pesticidal formulation & supersorbent | (0.75%) (0.1%) | (1) 93.0% (2) 74.0% |
| 100% water | | 0.0% |

EXAMPLE 3

The pesticidal preparations of Example 2 were prepared. In addition, a concentrated composition of the pesticidal agent admixed with supersorbent was prepared, aged for 10 days, and diluted to a ready-to-use formulation of 0.75% pesticidal formulation and 0.10% supersorbent. Fifty *Hypochoeris radicata* (false dandelion) plants were treated with these compositions and the plant damage after approximately 10 days was tabulated as follows.

| Treatment | | % Damage |
|---|---|---|
| 100% water | | 0.0% |
| pesticidal formulation alone | | 8.0% |
| pesticidal formulation | (0.75%) | (1) 20.0% |
| & 0.10% supersorbent | | (2) 24.0% |
| pesticidal formulation supersorbent (from aged concentrate) | (0.75%) & 0.10% | 50.0% |

EXAMPLE 4

A microemulsion formulation having Broadleaf P4 polyacrylamide supersorbent and a pesticidal agent consisting of pelargonic acid was prepared and diluted to ready-to-use formulations having pesticidal formulation concentrations of 0.50%, 0.625%, 0.70% and 0.875%. For each concentration level of pesticidal formulation the supersorbent concentration was varied between 0%, 0.002% and 0.10%. One hundred thirty *Hypochoeris radicata* (false dandelion) plants were treated with these pesticidal compositions and placed in a greenhouse. After approximately 7 days the plant damage was assessed and the results tabulated as follows.

| % Pesticidal Formulation | % PLANT DAMAGE BY Concentration of Supersorbent | | |
|---|---|---|---|
| | 0% | 0.002% | 0.10% |
| 0% | 0.0% | — | — |
| 0.5% | 10.0% | 6.0% | 12.0% |
| 0.625% | 5.0% | 15.0% | 62.0% |
| 0.70% | 7.0% | 11.0% | 86.0% |
| 0.875% | 31.0% | 59.0% | 98.0% |

EXAMPLE 5

A microemulsion formulation having Broadleaf P4 polyacrylamide supersorbent and a pesticidal agent consisting of pelargonic acid was prepared and diluted to ready-to-use formulations having pesticidal formulation concentrations of 0.25%, 0.5%, 0.625%, 0.70%, 0.875 and 1.0%. For each concentration level of pesticidal formulation, the supersorbent concentration was varied between 0.0%, 0.002% and 0.10%. In addition, a one month old formulation having 1.0% pesticidal formulation and 0.10% Broadleaf P4 was tested. Two hundred *Hypochoeris radicata* (false dandelion) plants were treated with these formulations and placed in a greenhouse. After approximately 7 days, plant damage was assessed and tabulated as follows:

| % Pesticidal Formulation | % PLANT DAMAGE BY Concentration of Supersorbent | | | |
|---|---|---|---|---|
| | 0% | 0.002% | 0.10% | 0.10%(aged) |
| 0% | 0.0% | — | — | — |
| 0.25% | 1.0% | 1.0% | 0.0% | — |
| 0.50% | 3.0% | 6.0% | 7.0% | — |
| 0.625% | 5.0% | 7.0% | 21.0% | — |
| 0.70% | 15.0% | 16.0% | 51.0% | — |
| 0.875% | 41.0% | 45.0% | 81.0% | — |
| 1.00% | 74.0% | 64.0% | 96.0% | 91.0% |

EXAMPLE 6

One hundred ninety *Hypochoeris radicata* (false dandelion) plants were selected and labelled into 19 treatments (10 replicates per treatment). Plants were of the same age and as uniform in growth development as possible. The growing medium was standard peat-vermiculite-sand mix in 5.5 cm square pots. The false dandelion plants were healthy, actively growing plants which were randomly assigned treatment solutions. The treatments consisted of pesticidal formulations having Paraquat (Gramoxone) alone and in combination with Broadleaf P4 polyacrylamide supersorbent. The treatments were applied having the lowest recommended paraquat dosage (0.0373%), as well as one-half (0.0187%), one-quarter (0.0093%) and one-eight (0.0047%) of the lowest recommended dosage. The pesticidal compositions were applied with a hand-held trigger sprayer with plants randomly placed within a one meter square area. To this area one hundred fifty milliliters of each treatment was evenly applied. The plants were allowed to dry and were then placed in a greenhouse and the plant damage was tabulated as follows.

| Conc. of Paraquat | % Plant Damage by Conc. of Supersorbent | |
|---|---|---|
| | 0.0% | 0.10% |
| 0% | 0.0% | — |
| 0.0373% | 96.0% | 98.0% |
| 0.0187% | 96.0% | 97.0% |
| 0.0093% | 87.0% | 90.0% |
| 0.0047% | 16.0% | 54.0% |

Having described the present invention, what is claimed is:

1. A pesticide composition comprising:
a pesticidally effective amount of an herbicide or fungicide selected from the group consisting of
Glyphosate (N-(phosphonomethyl) glycine); Alachlor (2-chloro-2',6'-diethyl-N-(methoxymethyl)-acetanilide); Ammonium sulfamate; Ammonium nitrate; ammonium sulfate; Atrazine (2-chloro-4-(ethylamino)-6-(isopropylamino)-s-triazine);
Chlorpropham (isopropyl m-chlorocarbanilate); Dicamba (3,6-dichloro-o-anisic acid); Dinoseb (2-sec-butyl-4,6-dinitrophenol); Paraquat (1,1'-dimethyl-4-4'-bipyridinium); Gramoxone (1,1'-dimethyl-4-4'-bipyridinium dichloride); Picloram (4-amino-3,5,6-trichloropicolinic acid); Simazine (2-chloro-4,6-bis(ethylamino)-s-triazine); Trifluralin [a,a,a-trifluoro-2,6-dinitro-N,N-dipropyl-p-toluidine); 2,4-D ((2,4-dichlorophenoxy) acetic acid); amine salts of 2,4-D; mineral salts of 2,4-D; esters of 2,4-D; straight-chained alpha monocarboxylic acids having 6–18 carbon salts of straight-chain alpha monocarboxylic acids having 6–18 carbon atoms; atoms; ammonium nitrate; ammonium sulfate; ammonium sulfamate;

Benomyl (methyl 1-(butylcarbamoyl)benzimidazol-2-ylcarbamate); Captafol (N-(1,1,2,2-tetrachloroethylthio)-3a, 4,7,7a-tetrahydrophothalimide; Captan (N-(trichloromethylthio)-3a-4,7,7a-tetrahydrophthalimide; Carboxin (2,3-dihydro-6-methyl-5-phenylcarbamoyl-1,4-oxathiin); Chlorothalonil (tetrachloroisophthalonitrile); Iprodione (3-(3,5-dichlorophenyl)-N-isopropyl-carbomoyl-2,4-dioxoimidazolidine-1-carboxamide); Maneb (manganese ethylenebisdithiocarbamate); Thiabendazole (2-(4-thiazol-4-yl) benzimidazol); Thiram (tetramethylthiuram disulphide); Zineb (zinc ethylenebisdithiocarbamate), and mixtures thereof;

a polyacrylamide supersorbent material able to absorb water in an amount at least 10 times its original weight; and an aqueous solvent.

2. The composition of claim 1 wherein said supersorbent material is able to absorb from 30 to 600 times its original weight in water.

3. The composition of claim 2 wherein said supersorbent material has a molecular weight ranging from 150,000 to 6 million daltons.

4. The composition of claim 3 wherein said supersorbent material is present in a concentration of about 0.01 to 0.5 parts of said pesticide composition.

5. The composition of claim 3 wherein said supersorbent material is present in a concentration ratio of approximately 0.1 part by weight per part of said pesticide composition.

6. The composition of claim 4 wherein the effective amount of the pesticidal component is less than the lowest efficacious dosage of the pesticidal component used alone.

7. The composition of claim 6 wherein the polyacrylamide supersorbent material is cross-linked.

8. The composition of claim 1 wherein the effective amount of said pesticidal component is about 0.0047% to about 0.0373% by weight.

9. The composition of claim 1 wherein the supersorbent material is present in a concentration of 0.10 part by weight per part of pesticidal composition.

10. The composition of claim 1 wherein the effective amount of the pesticidal component is 0.4% by weight.

11. The composition of claim 1 wherein the effective amount of the pesticidal formulation is about 0.625% to about 0.875% by weight.

12. The composition of claim 1 wherein the supersorbent is present in a concentration ratio of 0.10 part by weight per part of pesticidal composition.

13. A pesticide composition comprising:
a pesticidally effective amount of a pesticidal component selected from the group consisting of herbicides and fungicides;
a polyacrylamide supersorbent material having a molecular weight ranging from 150,000 to 6 million daltons, able to absorb water in an amount ranging from 30 to 600 times its original weight, and present in an a concentration of about 0.01 to 0.5 parts of said pesticide composition; and
an aqueous solvent,
wherein said pesticidal component comprises:
a first component selected from the group consisting of herbicidally active organic acids having between 6 and 18 carbon atoms, salts thereof and mixtures thereof; and
a second component selected from the group consisting of ammonium nitrate, ammonium sulfate and ammonium sulfamate, said pesticidal component having a ratio of the first component to the second component of between 0.01 and 5.0.

14. The composition of claim 5 wherein said insecticidal component comprises:
a first component selected from the group consisting of
insecticidally active unsaturated fatty acids having 18 carbon atoms, salts thereof and mixtures thereof; and
organic esters of phosphoric or thiophorphoric acid and carbamates, and mixtures thereof,
said unsaturated fatty acid component comprising at least 50% by weight of the mixture of the insecticidally active fatty acid component.

15. The method of improving the pesticidal activity of a surface-applied aqueous pesticide comprising applying an effective amount of said pesticide to the surface of a plant in admixture with a cross-linked polyacrylamide supersorbent material able to absorb at least 10 time its weight in water,
wherein said pesticide is selected from the group consisting of
Glyphosate (N-(phosphonomethyl) glycine); Alachlor (2-chloro-2',6'-diethyl-N-(methoxymethyl)-acetanilide); Ammonium sulfamate; Ammonium nitrate; ammonium sulfate; Atrazine (2-chloro-4-(ethylamino)-6-(isopropylamino)-s-triazine);
Chlorpropham (isopropyl m-chlorocarbanilate); Dicamba (3,6-dichloro-o-anisic acid); Dinoseb (2-sec-butyl-4,6-dinitrophenol); Paraquat (1,1'-dimethyl-4-4'-bipyridinium); Gramoxone (1,1'-dimethyl-4-4'-bipyridinium dichloride); Picloram (4-amino-3,5,6-trichloropicolinic acid); Simazine (2-chloro-4,6-bis(ethylamino)-s-triazine); Trifluralin [a,a,a-trifluoro-2,6-dinitro-N,N-dipropyl-p-toluidine); 2,4-D ((2,4-dichlorophenoxy) acetic acid); amine salts of 2,4-D; mineral salts of 2,4-D; esters of 2,4-D; straight-chained alpha monocarboxylic acids having 6–18 carbon atoms; salts of straight-chain alpha monocarboxylic acids having 6–18 carbon atoms; ammonium nitrate; ammonium sulfate; ammonium sulfamate;

Benomyl (methyl 1-(butylcarbamoyl)benzimidazol-2-benzimidazolcarbamate); Captafol (N-(1,1,2,2-tetrachloroethylthio)-3a, 4,7,7a-tetrahydrophthalimide; Captan (N-(trichloromethylthio)-3a4,7,7a-tetrahydrophthalimide; Carboxin (2,3-dihydro-6-methyl-5-phenylcarbamoyl-1,4-oxathiin); Chlorothalonil (tetrachloroisophthalonitrile); Iprodione (3-(3,5-dichlorophenyl)-N-isopropyl-carbomoyl-2,4-dioxoimidazolidine-1-carboxamide); Maneb (manganese ethylenebisdithiocarbamate); Thiabendazole (2-(4-thiazol-4-yl) benzimidazol); Thiram (tetramethylthiuram disulphide); Zineb (zinc ethylenebisdithiocarbamate);

(isoproply (2E, 4E)-11-methoxy-3,7,11-trimethyl-2, 4-dodecadienoate); (2, propynyl (2E, 4E)-3,7,11-trimethyl-2, 4-dodecadienoate); (N(((4-chlorophenyl)amino)carbonyl)-2, 6-difluorobenzamide); (N-(2-chloro-4-trifluoromethyl) phenyl)-DL-valine (alpha)-cyano)3-phenoxyphenyl) methyl ester); ((+)alpha-cyano-3-phenoxybenzyl(+)cis, trans-3(2,2-dichlorovinyl)-2,2-dimethyl cyclopropane-carboxylate); *Bacillus thuringiensis kurstaki; Bacillus thuringiensis tenebrionis;* (hexakis(beta,beta dimethylphenethyl)-distannoxane); (1-napthyl methylcarbamate); ((4-dimethylaminophenyl-3-methyl-phenyl)-N-methylcarbamate); *Bacillus thuringiensis san diego*, and mixtures thereof.

16. The method of claim 15 wherein the supersorbent material absorbs between 40 and 600 times its weight in water.

17. The method of claim 15 wherein said supersorbent has a molecular weight ranging from 150,000 to 6 million daltons.

18. The method of claim 17 wherein said supersorbent is present in a concentration ratio ranging from about 0.01 to 0.5 part by weight per part of pesticidal composition.

19. The method of claim 17 wherein said supersorbent is present at a concentration ratio of approximately 0.1 part by weight per part of formulation.

20. The method of claim 15 wherein said pesticide is a salt of pelargonic acid.

21. The method of claim 15 wherein said pesticide is a herbicide.

22. The method of claim 15 wherein said pesticide is a fungicide.

23. The method of claim 15 wherein said pesticide is an insecticide.

24. A method of protecting a plant from phytophagous insect infestation and damage, said method comprising the step of:
applying to the surface of the plant an insecticidally effective amount of a composition comprising an insecticide, a polyacrylamide supersorbent material able to absorb water in an amount at least 10 times its original weight, and an aqueous solvent.

25. The method of claim 24 wherein the supersorbent material absorbs between 40 and 600 times its weight in water.

26. The method of claim 24 wherein said supersorbent material has a molecular weight ranging from 150,000 to 6 million daltons.

27. The method of claim 26 wherein said supersorbent material is present in a concentration ratio ranging from about 0.01 to 0.5 parts by weight per part of pesticide composition.

28. The method of claim 26 wherein said supersorbent material is present at a concentration ratio of approximately 0.1 parts by weight per part of pesticide composition.

29. An insecticidal composition for application to a plant to protect the plant from insect infestation and damage wherein said insecticidal composition comprises:
an insecticidally effective amount of an insecticidal component selected from the group consisting of (isoproply (2E, 4E)-11-methoxy-3,7,11-trimethyl-2, 4-dodecadienoate); (2, propynyl (2E, 4E)-3,7,11-trimethyl-2, 4-dodecadienoate); (N(((4-chlorophenyl)amino)carbonyl)-2, 6-difluorobenzamide); (N-(2-chloro-4-trifluoromethyl) phenyl)-DL-valine (alpha)-cyano)3-phenoxyphenyl) methyl ester); ((+)-alpha-cyano-3-phenoxybenzyl(+)cis, trans-3(2,2-dichlorovinyl)-2,2-dimethyl cyclopropane-carboxylate); *Bacillus thuringiensis kurstaki; Bacillus thuringiensis tenebrionis;* (hexakis(beta,beta dimethylphenethyl)-distannoxane); (1-napthyl methylcarbamate); ((4-dimethylaminophenyl-3-methyl-phenyl)-N-methylcarbamate); *Bacillus thuringiensis san diego*, and mixtures thereof;
a polyacrylamide supersorbent material able to absorb water in an amount at least 10 times its original weight; and
an aqueous solvent.

30. The composition of claim 29 wherein said supersorbent material is able to absorb from 30-600 times its original weight in water.

31. The composition of claim 30 wherein said supersorbent material has a molecular weight ranging from 150,000 to 6 million daltons.

32. The composition of claim 31 wherein said supersorbent material is present in a concentration of about 0.01 to 0.5 parts of said pesticide composition.

33. The composition of claim 31 wherein said supersorbent material is present in a concentration ratio of approximately 0.1 parts by weight per part of said pesticide composition.

34. The composition of claim 32 wherein the effective amount of said pesticidal component is less than the lowest efficacious dosage of said pesticidal component used alone.

35. The composition of claim 34 wherein the polyacrylamide supersorbent material is cross-linked.

* * * * *